US00PP37036P2

(12) United States Plant Patent
Cain

(10) Patent No.: US PP37,036 P2
(45) Date of Patent: Oct. 21, 2025

(54) GRAPEVINE PLANT NAMED 'BLOMG06'

(50) Latin Name: *Vitis vinifera*
Varietal Denomination: BLOMG06

(71) Applicant: BLOOM FRESH INTERNATIONAL LIMITED, London (GB)

(72) Inventor: David Cain, Lutz, FL (US)

(73) Assignee: BLOOM FRESH INTERNATIONAL LIMITED, London (GB)

( * ) Notice: Subject to any disclaimer, the term of this patent is extended or adjusted under 35 U.S.C. 154(b) by 0 days.

(21) Appl. No.: 19/053,502

(22) Filed: Feb. 14, 2025

(51) Int. Cl.
*A01H 5/08* (2018.01)
*A01H 6/88* (2018.01)

(52) U.S. Cl.
USPC ..... Plt./205
CPC ..... *A01H 6/88* (2018.05); *A01H 5/08* (2013.01)

(58) Field of Classification Search
USPC ..... Plt./157, 205
See application file for complete search history.

(56) References Cited

U.S. PATENT DOCUMENTS

PP23,125 P2 * 10/2012 Sheehan ..... A01H 6/88 Plt./205
PP26,121 P3 11/2015 Cain
PP28,956 P2 2/2018 Cain

OTHER PUBLICATIONS

U.S. Appl. 18/951,196, filed Nov. 18, 2024, by Cain et al. (Copy not submitted herewith pursuant to the waiver of 37 C.F. R. § 1.98(a)(2)(iii) issued by the Office on Oct. 19, 2004).

* cited by examiner

*Primary Examiner* — Karen M Redden
(74) *Attorney, Agent, or Firm* — Michael Best & Friedrich LLP

(57) ABSTRACT

Described herein is a new distinct variety of grapevine plant named 'BLOMG06'. 'BLOMG06' is characterized by producing medium sized narrow ellipsoid red berries having very crisp texture with a with a sweet neutral flavor that ripens in late season. Berries are borne on medium size clusters which are loose and do not require gibberellin applications to thin clusters. Gibberellin is required to increase berry size.

1 Drawing Sheet

Latin name of the genus and species claimed: *Vitis vinifera.*

Variety denomination: 'BLOMG06'.

BACKGROUND OF THE INVENTION

Described herein is a new distinct variety of grapevine plant name described 'BLOMG06'. The 'BLOMG06' variety originated from a hand pollinated cross of '06143-076-002' (an unpatented, unreleased numbered selection) and 'IFG Twenty-four' (U.S. Plant Pat. No. 28,956) hybridized in May 2013. The abortive seed traces were subsequently embryo cultured, and the resulting 243 seedlings were planted in the field in April 2014. The present variety of grapevine was selected as a single plant in September 2016 and was asexually propagated by hardwood cuttings in December 2016, grafting on 'Freedom' (unpatented virus free rootstock), near Delano, Kern County, California. These resulting propagules were planted during April 2017 near Delano, Kern County, California and were found to reproduce true-to-type through at least two generations of asexual propagation.

SUMMARY

The new grapevine plant 'BLOMG06' is characterized by producing medium sized narrow ellipsoid red berries having very crisp texture with a sweet neutral flavor. Fruit normally ripens late-season approximately 4-weeks after 'Thompson Seedless' (not patented) in California. Berries are borne on medium size clusters which are loose and do not require gibberellin applications to thin clusters. Gibberellin is required to increase berry size. 'BLOMG06' stores well. Stems remain green and berries retain their crisp texture and strong flavor for up to eight weeks in cold storage.

'BLOMG06' is most similar to 'Sheegene 20' (U.S. Plant Pat. No. 23, 125). 'BLOMG06' differs from 'Sheegene 20' by the natural berry weight, the berry firmness, and the thickness of the skin. 'BLOMG06' produces natural berries about 8 g, where 'Sheegene 20' produces natural berries about 11.36 g. The texture of the berries of 'BLOMG06' is very firm, while the texture of the berries of 'Sheegene 20' is firm. The berries of 'BLOMG06' have a thin skin (0.7 mm) where the berries of 'Sheegene 20' have a medium skin thickness (.

'BLOMG06' differs from its maternal parent, 'IFG Twenty-four' by maturing several weeks earlier in the growing season, and by having less berry shatter pre-harvest and post-harvest than 'IFG Twenty-four'. Clusters of 'BLOMG06' are smaller than 'IFG Twenty-four'.

'BLOMG06' differs from its seed parent '06143-076-002', by ripening about three to four weeks later, and by having red berries instead of white berries.

BRIEF DESCRIPTION OF THE DRAWING OR PHOTOGRAPHS

The accompanying color photographs illustrate the overall appearance of the 'BLOMG06' plant showing the colors as true as it is reasonably possible to obtain in colored reproductions of this type. Colors in the photographs may differ slightly from the color values cited in the detailed botanical description that accurately describe the colors of the plant described herein. These figures are exemplary will vary depending on the plant and distinguishing characteristics.

FIG. 1 shows the form, foliage, and fruit of a 4-year old 'BLOMG06' vine grown in the field at McFarland, Kern County, California. The left side of the figure has a mature leaf. A mature fruit cluster is represented in the center of the figure along with a typical berry in cross section. A young shoot tip (4 weeks) can be seen on the right side of the figure. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon a reprint of The R.H.S. Colour Chart, published in 2016 by The Royal Horticultural Society, London, England.

Throughout this specification, subjective description values conform to those set forth by the International Union for the Protection of New Varieties of Plants (UPOV) publication TG/50/10 "Grapevine *Vitis* L. Guidelines for the Conduct of Tests for Distinctness, Uniformity, and Sustainability" Geneva (2023).

The descriptive matter which follows pertains to 4-year old 'BLOMG06' plants grown in the vicinity of McFarland, Kern County, California during 2023 and 2024, and is believed to apply to plants of the variety grown under similar conditions of soil and climate elsewhere:

Classification:

*Family*.—Vitaceae.

*Botanical*.—*Vitis vinifera*.

*Common name*.—Grapevine.

*Cultivar name*.—'BLOMG06'.

Plant:

*Plant habit and growth*.—Erect.

*Vigor*.—Medium vigor; under similar climatic and nutritional conditions, the thickness of the trunk and the wood shoots are moderate.

*Density of foliage*.—Medium.

*Productivity*.—Very productive, producing about 48 kg of fruit per vine.

*Plant hardiness zone*.—Fully hardy in USDA zone 9A (2012). Not tested in other zones.

*Root stock*.—'Freedom'.

*Training method*.—Typically spur pruned leaving 2 bud spurs.

Trunk:

*Size*.—Diameter of 4-year-old vines at 30 cm above the soil line — Approximately 4.87 cm.

*Shape*.—Short split.

*Surface texture*.—Medium rough texture.

*Bark color*.—Inner bark color — Greyed-orange: 166A and 166B. Outer bark color — Greyed-green: 197C.

Shoots:

*Young shoot* (4-*weeks*).—

*Form of tip*.—Half open.

*Distribution of anthocyanin coloration of tip*.—Absent.

*Intensity of anthocyanin coloration of tip*.—Absent.

*Density of prostrate hairs of tip*.—Very sparse.

*Density of erect hairs on tip*.—Absent.

*Color*.—Yellow-green: 144B.

Woody shoot (mature canes):

*Internode length*.—Long: About 8 cm.

*Width at node*.—About 1.04 cm.

*Cross section*.—Circular.

*Surface*.—Striate.

*Main color*.—The following colors were observed: Greyed-orange: 166B and 166C.

*Density of erect hairs on nodes*.—None or very sparse.

*Density of erect hairs on internodes*.—None or very sparse.

*Axillary shoot vigor at full bloom*.—Medium: Approximately 11.8 cm long.

Flowering shoot:

*Vigor during flowering*.—Moderately vigorous.

*Attitude during flowering on shoots not tied*.—Semi erect.

*Color*.—Dorsal side of internodes — Yellow-green: 144B.

*Color*.—Ventral side of internodes — Yellow-green: 144A.

*Color*.—Dorsal side of nodes — Yellow-green: 144A.

*Color*.—Ventral side of nodes — Yellow-green: 144A.

*Density of prostrate hairs on nodes*.—Very sparse.

*Density of erect hairs on nodes*.—None.

*Density of prostrate hairs on internode*.—None.

*Density of erect hairs on internode*.—None.

*Anthocyanin coloration of buds*.—Absent.

Tendrils:

*Distribution on the shoot* (*at full flowering*).—Discontinuous.

*Length of tendril*.—Medium: About 21.5 cm.

*Thickness of tendril* 2 *cm from base*.—About 2.4 mm.

*Color*.—The following colors were observed: Yellow-green: 144A.

*Form*.—Non-forked and bifurcated.

*Number of consecutive tendrils*.—2.

Leaves:

*Young leaves*.—Color of upper surface of first four distal unfolded leaves — Yellow-green: 144A. Color of lower surface of young leaves — Yellow-green: 144A. Average intensity of anthocyanin coloration of six distal leaves prior to flowering — Absent. Density of prostrate hairs between veins (lower surface) — Absent. Density of prostrate hairs on veins (lower surface) — Sparse medium. Density of erect hairs between veins (lower surface) — Absent. Density of erect hairs on veins (lower surface) — Absent.

*Mature leaves* (*opposite first cluster*).—Average length — About 15.7 cm. Average width — About 17.2 cm. Mature leaf size — Medium. Shape of blade — Pentagonal. Number of lobes — 5. Blade venation — Palmate. Anthocyanin coloration of main veins on upper side of blade — Absent. Mature leaf profile — V-shaped. Blistering surface of blade upper surface — Very weak. Leaf blade tip — In the horizontal plane of the leaf mid-vein. Does not appear to curve downward. Leaf apex — Acute. Leaf margin — Serrate. Undulation of margin — Slight. Undulation of blade between main and latera l veins — Slight undulation over entire area. Shape of teeth — Mixture of both sides straight and both sides convex. Length of teeth — About 2-15 mm. Width of teeth — About 12.1 mm. Ratio length/width of teeth — Medium. Shape of upper lateral sinuses — Lobes slightly overlapping. Depth of upper lateral sinuses — Medium. General shape petiole sinus — Closed. Shape of base of upper leaf sinuses — V-shaped. Tooth at petiole sinus — Absent. Density of prostrate hairs between veins on lower surface of blade — Very sparse. Density of erect hairs between veins on lower surface of blade — Absent. Density of prostrate hairs on main veins on lower surface of blade — Very sparse. Density of erect hairs on main veins on lower surface of blade — Absent. Density of prostrate hairs on main veins on upper surface of blade — Very sparse. Density of erect hairs on main veins on upper surface of blade — Absent. Autumn coloration of leaves — Greyed-yellow group 162A and 162B.

*Upper surface*.—Color — Green: 137A. Anthocyanin coloration of main veins (upper surface) — Absent. Color of main veins — Green: 137D. Surface appearance — Semi-glossy. Blistering surface of blade — Very weak.

*Lower surface*.—Color — Green: 138B. Anthocyanin coloration of main veins (lower surface) — Absent. Color of main veins — Green: 139D. Glossiness — Weak. Surface texture — Smooth. Surface appearance — Semi-glossy.

Petiole:

*Length*.—About 15.8 cm.

*Diameter of petiole* 2 *cm from blade*.—About 2.2 mm.

*Petiole color*.—The following colors were observed: Yellow-green: 144D.

*Length of petiole compared to middle vein*.—Equal.

*Density of prostrate hairs on petiole*.—None to very sparse.

*Density of erect hairs on petiole*.—None to very sparse.

Buds:

*Bud fruitfulness*.—Basal: mostly fruitful.

*Position of first fruitful shoot on previous season cane*.—$1^{st}$ to $2^{nd}$ node.

*Dormant bud length*.—About 6.1 mm.

*Dormant bud width in the proximal/distal plane*.—About 3.87 mm.

*Dormant bud color*.—Greyed-orange group 166A, 166B.

*Time of bud burst*.—Mid-season: About Mar. 15, 2024.

Flowers:

*General*.—Flower sex — Hermaphrodite. Length of single flower, unopened — About 2.6 mm. Width of single flower — Unopened: About 1.6 mm. Opened: About 4.7 mm. Stamen length — About 2.6 mm. Stamen count — 5, occasionally 6. Pollen color — Yellow group 5D. Pistil length — About 1.7 mm. Pistil color — Green group: 143A. Length of first inflorescence — Medium to long: About 25.9 cm long by 10.1 cm wide. Position of first flowering and fruiting node — $3^{rd}$ node. Number of inflorescences per flowering shoot — 1.1 to 2. Time of bloom — Midseason as compared with similar varieties in the growing area of McFarland, California. Date of full bloom — About May 5, 2024.

Fruit:

*General*.—Ripening period — Late: Approximately Sep. 25, 2024. Use — Fresh market. Keeping quality — Stems remain green, and berries retain their crisp texture and strong flavor for up to eight weeks in cold storage. Refractometer test — Soluble solids: About 18.2 Brix. Brix/acid — About 50.56. Titratable acidity — About 0.36%. Juice pH — About 4.6. Juice color — Yellow-green: 150D.

*Cluster*.—Mature cluster length (peduncle excluded) — About 24.3 cm. Mature cluster width — About 11.9 cm. Mature cluster weight — About 976.2 g. Bunch density — Medium: densely distributed berries, pedicels not visible, berries movable. Number of berries — About 137.Form — Conical.

*Peduncle*.—Lignification of peduncle — Medium. Diameter of peduncle — Approximately 4.4 mm. Length of peduncle — Short: Approximately 6.16 cm. Color of peduncle — Yellow-green: 145A.

*Berry*.—Uniformity of size — Uniform. Single berry weight — About 8 g natural; to about 13.65 g when treated with gibberellic acid. Shape — Narrow ellipsoid. Seeds — Absent. Cross section — Circular. Berry dimensions: Longitudinal axis: about 3.31 cm. Horizontal axis: about 1.88 cm. Pedicel: Length — About 6.6 mm. Width — About 1.44 mm. Color — Yellow-green: 145A. Berry firmness — very firm. Flavor — neutral. Bloom (cuticular wax) — Strong. Berry separation from pedicel — Difficult. Skin color (without bloom) — Greyed-purple group 187C. Flesh color — Yellow-green: 145D. Anthocyanin color of flesh — Absent. Skin: Thickness — Thin, about 0.7 mm. Skin toughness — Somewhat notable when chewing. Reticulation — Absent. Tenacity — Tenacious to flesh.

Disease and insect resistance:

*Resistance/susceptibility to typical pests and disease of Vitis vinifera species*.—Not observed to date.

What is claimed:

1. A new and distinct variety of grapevine plant named 'BLOMG06' as substantially described and illustrated herein.

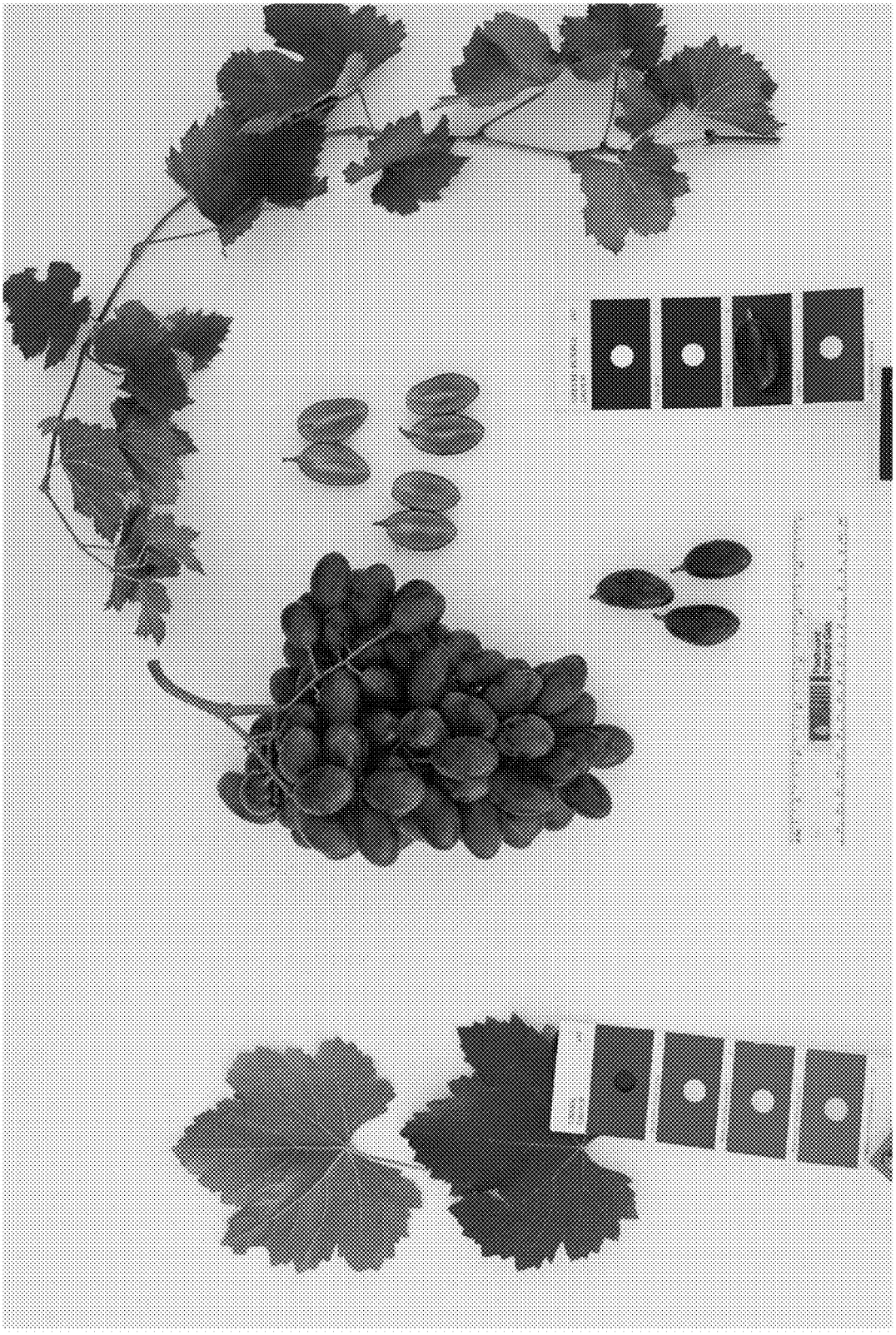

* * * * *